United States Patent
Quigley et al.

(10) Patent No.: US 8,062,346 B2
(45) Date of Patent: Nov. 22, 2011

(54) FLEXIBLE STENT-GRAFT DEVICE HAVING PATTERNED POLYMERIC COVERINGS

(75) Inventors: Fergus Quigley, Seattle, WA (US); Robert C. Thistle, Bridgewater, MA (US); William Quinn, Swampscott, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 82 days.

(21) Appl. No.: 12/338,904

(22) Filed: Dec. 18, 2008

(65) Prior Publication Data

US 2009/0163994 A1   Jun. 25, 2009

Related U.S. Application Data

(60) Provisional application No. 61/016,160, filed on Dec. 21, 2007.

(51) Int. Cl.
*A61F 2/82* (2006.01)
(52) U.S. Cl. .................................. 623/1.13; 623/1.22
(58) Field of Classification Search ............... 623/1.1, 623/1.12, 1.13, 1.17
See application file for complete search history.

(56) References Cited

U.S. PATENT DOCUMENTS

| | | |
|---|---|---|
| 4,503,569 A | 3/1985 | Dotter |
| 4,580,568 A | 4/1986 | Gianturco |
| 4,732,152 A | 3/1988 | Wallsten et al. |
| 4,733,665 A | 3/1988 | Palmaz |
| 4,856,561 A | 8/1989 | Zicaro |
| 4,886,062 A | 12/1989 | Wiktor |
| 5,462,781 A | 10/1995 | Zukowski |
| 5,466,509 A | 11/1995 | Kowligi et al. |
| 5,700,285 A | 12/1997 | Myers et al. |
| 5,733,925 A | 3/1998 | Kunz et al. |
| 5,735,892 A | 4/1998 | Myers et al. |
| 5,876,448 A | 3/1999 | Thompson et al. |
| 5,928,279 A * | 7/1999 | Shannon et al. ............. 623/1.13 |
| 6,344,054 B1 | 2/2002 | Parodi |
| 6,361,637 B2 | 3/2002 | Martin et al. |
| 6,398,803 B1 | 6/2002 | Layne et al. |
| 6,673,103 B1 | 1/2004 | Golds et al. |
| 6,716,239 B2 | 4/2004 | Sowinski et al. |
| 6,780,497 B1 | 8/2004 | Walter |
| 2002/0035396 A1 | 3/2002 | Heath |
| 2003/0017775 A1 | 1/2003 | Sowinski et al. |
| 2003/0220682 A1 | 11/2003 | Kujawski |
| 2004/0182511 A1 | 9/2004 | Rakos et al. |
| 2005/0113905 A1 * | 5/2005 | Greenberg et al. .......... 623/1.16 |
| 2008/0172121 A1 * | 7/2008 | Scholz et al. ............... 623/1.13 |

FOREIGN PATENT DOCUMENTS

| | | |
|---|---|---|
| WO | 00/018328 | 4/2000 |
| WO | 02/091949 | 11/2002 |
| WO | 2005/034806 | 4/2005 |
| WO | 2007/041010 | 4/2007 |
| WO | 2007/100455 | 9/2007 |
| WO | 2007/100456 | 9/2007 |

* cited by examiner

*Primary Examiner* — William H. Matthews
(74) *Attorney, Agent, or Firm* — Vidas, Arrett & Steinkraus (57) ABSTRACT

The present invention provides an endoprosthesis comprising a radially distensible, tubular stent comprising opposed open ends and a stent wall structure having opposed exterior and luminal surfaces; and a continuous and seamless ePTFE tubular covering having a node and fibril structure securably disposed to at least one of the stent surfaces, the graft covering comprising at least two laminated layers, wherein the laminated layers include at least one region where the laminated layers are not securely bonded; and the at least one region has a different bending flexibility from the tubular graft covering.

10 Claims, 4 Drawing Sheets

FLEXIBLE STENT-GRAFT DEVICE HAVING PATTERNED POLYMERIC COVERINGS

CROSS REFERENCE TO RELATED APPLICATION

This patent application claims priority to and the benefit of U.S. Provisional Patent Application No. 61/016,160 filed Dec. 21, 2007.

FIELD OF THE INVENTION

The present invention relates generally to an implantable prosthesis used to repair or replace a body lumen. More particularly, the present invention relates to an endoluminal prosthesis including a stent and ePTFE graft composite device offering increased compliance and flexibility.

BACKGROUND OF THE INVENTION

An endoluminal prosthesis is a medical device commonly known to be used in the treatment of diseased blood vessels. An endoluminal prosthesis is typically used to repair, replace, or otherwise correct a damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents generally include an open flexible configuration. Furthermore, this configuration allows the stent to be configured in a radially compressed state for intraluminal catheter implantation. Once properly positioned adjacent to the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures which have been used as intraluminal vascular stents have included coiled stainless steel springs; helically wound coils which may have undulations or zig-zags therein, slotted stents, ring stents, braided stents and open mesh wire stents, to name a few. Super-elastic materials and metallic shape memory materials have also been used to form stents.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of material, including textiles, and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels. In vascular applications, the grafts are manufactured from expanded PTFE (ePTFE) tubes. These tubes have a microporous structures which may allow natural tissue in growth and cell endothelization once implanted in the vascular system. This contributes to long term healing and patency of the graft.

A stent and a graft may be combined into a stent-graft endoprosthesis to combine the features and advantages of each. For example, tubular coverings have been provided on the inner and/or outer surfaces of stents to form the stent-graft. It is often desirable to use a thin-walled graft or covering in the stent-graft endoprosthesis to minimize the profile of the endoprosthesis and to maximize the flow of blood through the endoprosthesis. In such cases, non-textile materials, such as polymeric tubes or sheets formed into tubes, are often used. Expanded polytetrafluoroethylene or e-PTFE is one common polymeric material used as the graft portion or covering of a stent-graft endoprosthesis. Expanded polytetrafluoroethylene grafts, however, are subject to plastic deformation, especially:1) when compressing the stent-graft for loading into the delivery system, 2) delivering the stent-graft through a highly tortuous bodily lumen and 3) during placement/deployment at the target implant site. Such plastic deformation may lead to the tearing of the ePTFE, leaving the stent-graft endoprosthesis prone to leakage of blood therethrough. Furthermore, plastic deformation of expanded polytetrafluoroethylene grafts may lead to physical deformities in the graft, such as buckling, which is also undesirable because it may lead to poor blood flow patterns.

Sheets or films of ePTFE have been used to cover or line stents. For example, U.S. Pat. Nos. 5,700,285 and 5,735,892 to Myers et al. describe overlapping a sheet of ePTFE onto a stent to form a tubular graft. The graft is secured to the stent by an application of thermoplastic adhesive and heat treatment to melt the adhesive. A seam., which is formed where the sheet overlaps, is also sealed through the use of the thermoplastic adhesive. Such stent-grafts having a unitary tubular ePTFE covering adhesively secured to the stent, however, do not have differential flexibility associated with the graft to augment bending or plastic deformation of the graft when subjected certain stresses, such as bending stresses during delivery through tortuous bodily lumens or loading into a delivery system.

U.S. Pat. No. 6,361,637 to Martin et al. describes the securement or interweaving of ePTFE graft strips through helical windings of an undulating stent wire. The ePTFE strips are spaced apart from the apices of the undulating wire such that no strip completely covers a winding of the undulating wire. The graft strips are secured to the stent wire by use of a thermoplastic adhesive and the application of heat. While such a resulting stent-graft may have additional flexibility as compared to the above-described stent-grafts to Myers et al., the graft wall is non-continuous, thereby not providing by it self a fluid tight graft wall.

Apertures have also been imparted into the walls of tubular ePTFE grafts to increase flexibility. For example, U.S. Pat. No. 6,673,103 to Golds et al. describes a composite stent-graft tubular prosthesis which includes an inner PTFE tubular structure, an outer PTFE tubular structure positioned about the inner PTFE tubular structure and a diametrically deformable stent interposed between the inner and outer PTFE tubular structures. Portions of the stent are exposed exteriorly via apertures in the outer PTFE structure to render the composite prosthesis longitudinally flexible. Moreover, U.S. Pat. No. 6,398,803 to Layne et al. described partially encapsulated stents which are made by using gaps or slits cut into ePTFE covering material. By selecting the size and position, of the apertures or slits in the ePTFE covering, the '803 Patent describes that it is possible to leave certain parts of the stent unencapsulated to facilitate flexibility and expansion of the device. While such stent-grafts may have additional flexibility as compared to the above-described stent-grafts to Myers et al., the graft walls are not continuous, thereby not providing by itself a fluid tight graft wall.

U.S. Pat. No. 6,344,054 to Parodi describes a stent graft having its graft being secured to only one end of the stent. Such a graft avoids undue stresses being placed on the graft during contraction and expansion of the stent by only securing one end of the graft to the stent.

U.S. Patent Application Publication No. 2003/0220682 to Kujawski describes a hybrid braided stent having a plurality of overlapping graft segments. The graft segments are described as being textile graft segments made by, for example, braiding yarns. One end of a graft segment is secured to the stent, and the other end of the graft segment overlaps an adjacent secured graft segment.

Furthermore, ePTFE surfaces have been modified to alter porosity. For example, U.S. Pat. No. 5,466,509 to Kowligi et al. described a more porous ePTFE which is obtained by impressing a pattern, into extruded PTFE and then expanding the PTFE. The pattern is described as being impressed by knurling or rolling a sheet of PTFE sheet between rollers having a pattern formed on the surface of the roller. A roller with a coarse pattern is described as producing a wider distribution of internodal distances of the ePTFE as compared to a finer pattern, thereby increasing the porosity of the ePTFE material.

U.S. Pat. No. 5,462,781 to Zukowski describes an implantable porous expanded polytetrafluoroethylene material having a microstructure of nodes interconnected by fibrils where its surface has been modified by the removal of fibrils so that under magnification the surface has the appearance of freestanding node portions not interconnected by fibrils but rather having open valleys disposed between the freestanding node portions. Unmodified material beneath the surface is described as maintaining the original microstructure of nodes interconnected by fibrils. The modification is described as being done by exposing the surface to radio frequency gas plasma discharge with a reactive etching gas. The modified surface is described as having increased hydrophobicity. Such a modified surface is described as having improved blood contact properties and tissue in growth characteristics useful as an implantable device, such as a breast prosthesis.

U.S. Pat. No. 6,780,497 to Walter describes a process for surface treating ePTFE. The described process employs a laser to surface-modify an ePTFE structure to create a macro-roughened surface that has is described as being highly porous and modified to be highly textured or having increased roughness to promote tissue in growth.

While these later patents describe surface modification or ePTFE to increase porosity or surface modification to increase tissue in growth characteristics, these patents fail to describe modification of ePTFE to improve bending characteristics or to improve flexibility of the ePTFE material as compared to untreated ePTFE, The endovascular placement of vascular grafts is however subject to several physical performance requirements. One physical performance requirements in particular, is flexibility of the graft or stent/graft combination to permit the device to conform to artery/device angulation and tortuosity. This factor is highlighted especially when the graft or stent/graft combination is implanted in a particular location that requires it to conform to a curved radius of a particular vascular configuration. Typical grafts or stent/graft combinations may not always be flexible enough in the desired location. Stent/graft flexibility is typically a compromise between outward radial expansive force and longitudinal stiffness. Therefore, it is usually desirable that the graft or stent/graft combination have greater flexibility in only a certain defined region. In that way the graft will not compromise its overall structural integrity in order to provide adequate flexibility for certain regions.

For these reasons, it would be desirable to provide an improved prostheses which can overcome some of the drawbacks described above. In particular, it would be desirable to provide intraluminal prostheses which would provide a generally uniform structural integrity, while being able to provide enhanced flexibility in certain defined regions to accommodate and conform to the natural contours of the vasculature in which it is implanted.

SUMMARY OF THE INVENTION

One advantage of the present invention is that it provides an endoluminal prosthesis including a stent covered with a graft providing increased longitudinal flexibility, especially within certain defined regions.

The graft may be made from polymeric graft material, such as a polyester, a polypropylene, a polyethylene, a polyurethane, a polynaphthalene, a polytetrafluoroethylene, an expanded polytetrafluoroethylene, a silicone, and combinations and copolymers thereof.

Desirably, the graft is made from a laminated expanded polytetrafluoroethylene. During lamination, there are areas created within the lamination wherein the sintering and consolidation of the expanded polytetrafluoroethylene is affected by dimples in the ePTFE layer. The dimples are formed during the lamination process when air is evacuated through small holes in the lamination mandrel. The dimpled regions thus have lower stiffness and permeability. By exploiting the change in stiffness due to the dimples, a graft can be produced having a particular pattern of dimples to produce regions of increased flexibility.

The prosthesis of this aspect of the present invention may further include a radially distensible, tubular stent. Desirably, the stent comprises a plurality of undulating stent segments, for example an undulating wire helically wound into a plurality of circumferential windings to define a stent wall structure. The ePTFE graft may be securably attached to at least one of the circumferential windings of the undulating wire and having regions of the ePTFE graft is disposed between at least two adjacent windings of the circumferential windings of the undulating wire. Desirably, the substantially smooth tubular wall is free of folds, crimps and pleats.

In some embodiments, the present invention provides an endoprosthesis comprising a radially distensible, tubular stent comprising opposed open ends and a stent wall structure having opposed exterior and luminal surfaces; and a continuous and seamless ePTFE tubular covering having a node and fibril structure securably disposed to at least one of the stent surfaces, the graft covering comprising at least two laminated layers, wherein the laminated layers include at least one region where the laminated layers are not securely bonded; and the at least one region has a different bending flexibility from the tubular graft covering.

In another aspect of the present invention, a method of making a stent-graft having increased bending flexibility is provided. In the efficient attainment of these and other objectives, the method of this aspect of the present invention comprises providing a radially distensible, tubular stent comprising opposed open ends and a stent wall structure having opposed exterior and luminal surfaces, providing a continuously uninterrupted ePTFE tubular graft, the graft securably disposed to one of the stent surfaces, the graft comprising a continuously uninterrupted tubular wall comprising at least two laminated layers, providing at least one region where the laminated layers are not securely bonded; and the at least one region has a different bending flexibility from the tubular graft covering.

DETAILED DESCRIPTION OF THE PREFERRED EMBODIMENTS

The following is a detailed description of the preferred embodiments of the present invention. The description is meant to describe the preferred embodiments, and is not meant to limit the invention in any way.

Figure 1:
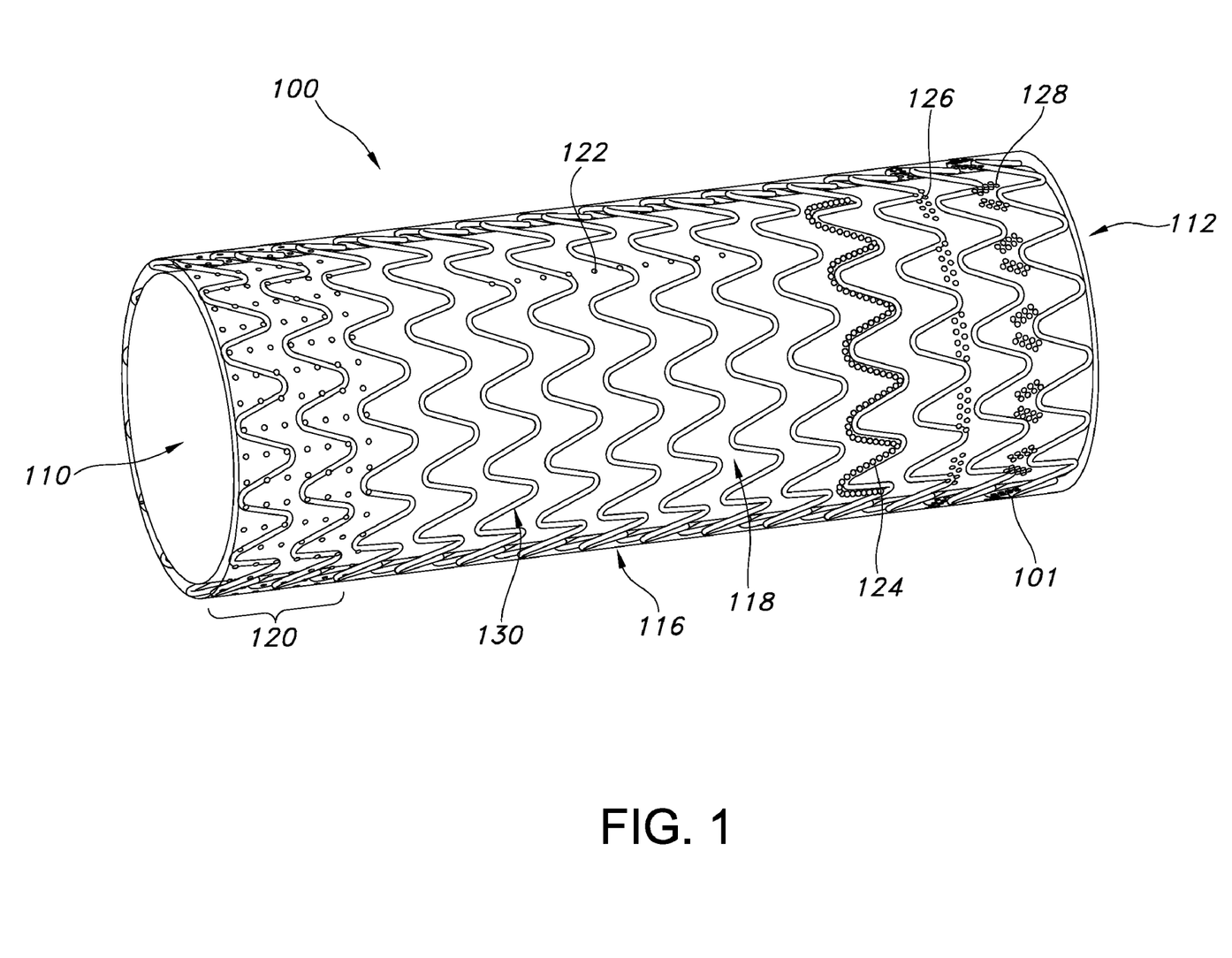
FIG. 1 shows a perspective view of a portion of an endoluminal prosthesis of the present invention.

FIG. 1 is a perspective view of a stent-graft 100 having enhanced flexibility of the present invention. The stent-graft 100 is a hollow, tubular structure or device having opposed open ends 110, 112. The stent-graft 100 includes a tubular wail 116 disposed between the open ends 110, 112. As depicted in FIG. 1, the tubular wall 116 extends along the longitudinal direction. The tubular wall 116 includes a graft 118 having plurality graft portions or regions 120, 122, 124, 126 and 128 that, as described below, have varied or different flexibilities, such as bending flexibilities and will be further described with reference to FIG. 2. The graft wall 116 also extends around the circumference of the stent-graft 100. The tubular wall further includes a stent device 130, which will be further explained and described with reference to FIG. 2 below. As depicted in FIG. 1, stent-graft 100 is a substantially longitudinally straight tubular device, but the present invention is not so limited. Stent-graft 100 may have a varying radial extent, for example, a varied diameter, outwardly or inwardly flared extents, and the like.

Figure 2:
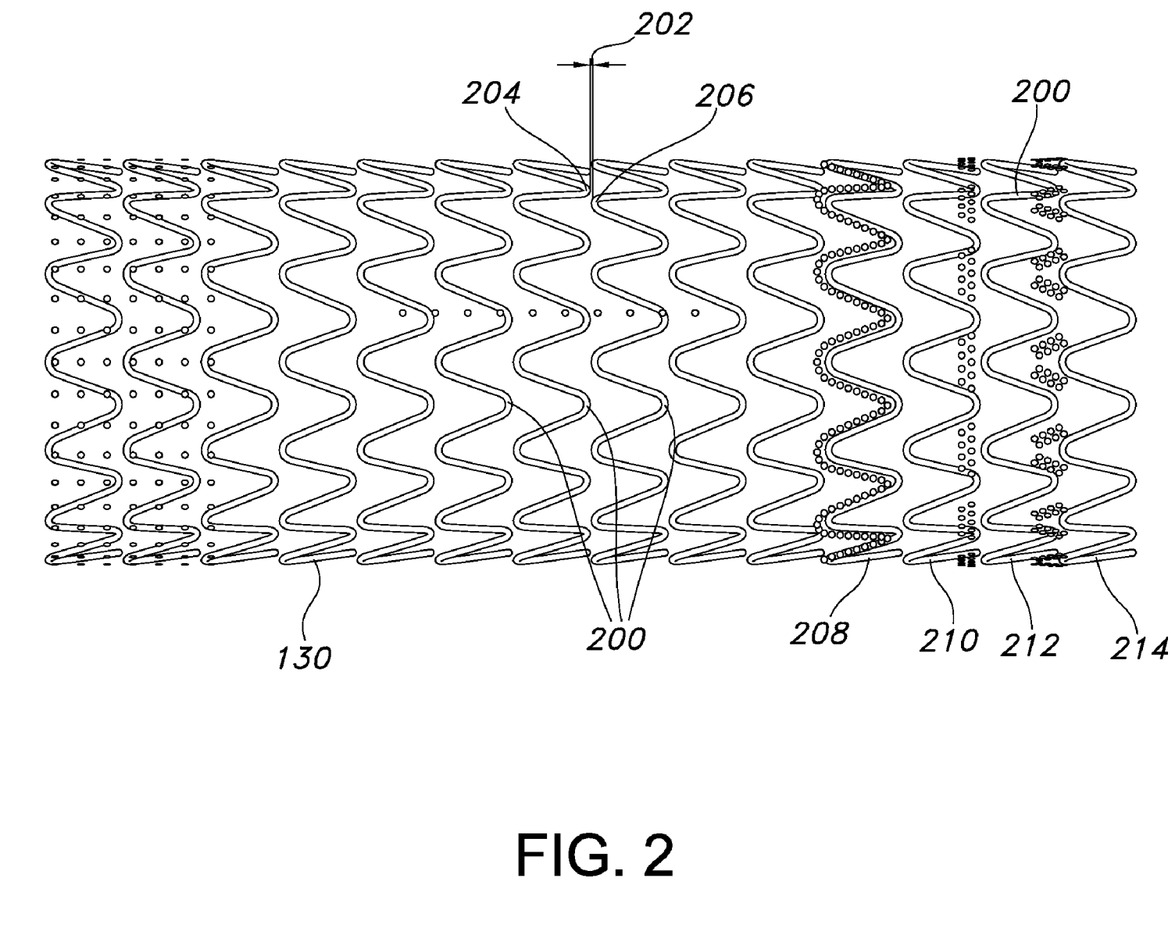
FIG. 2 shows a longitudinal side view of a portion of an endoluminal prosthesis of the present invention.

FIG. 2 is a side view of the stent-graft 100 of FIG, 1. As depicted in FIG. 2, the stent-graft 100 may include a stent 130. Various stent types and stent constructions may be employed in the invention as the stent 130. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in. spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern), with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. Nos. 4,503,569 to Dorter; 4,733,665 to Palmaz; 4,856,561 to Hillstead; 4,580,568 to Gianturco; 4,732,152 to Wallsten, 4,886,062 to Wiktor, and 5,876,448 to Thompson, all of whose contents are incorporated herein by reference.

Desirably, stent 130 is one that has minimal foreshortening, i.e., a stent wherein its longitudinal length remains substantially constant upon radial expansion or radial contraction of the stent. As depicted in FIG. 2, such a stent 130 having minimal foreshortening may include undulating stent portions. As depicted in FIG. 2, the stent 130 is primarily an undulating pattern having peaks 200 of the undulating stent which may be substantially longitudinally aligned. Further, the undulating stent portions 200 may be longitudinally offset from one and the other by a length, 202. For example, the peaks 204 of one undulating stent portion 130 may be longitudinally offset from the valleys 206 of an adjacent undulating stent portion 130 by a distance 202. Any suitable offset length, 202 may be used with the present invention. Desirably, the offset, 202, is less than the longitudinal length defined by the longitudinal distance from the peak 204 and the valley 206 of the undulating stent portion 130. In another aspect, as will be further described with respect to FIG. 4, nested undulating stent portions 131 may be useful as the stent 130 of the present invention.

As depicted in FIG. 1, the tubular wall 116 of graft 100 includes graft regions 120, 122, 124, 126 and 128 that have different bending flexibilities and are disposed at different locations along the stent-graft 100. The regions depicted, represent areas of dimples 101, which are more fully described with respect to FIGS. 3A, 3B and 3C, in the ePTFE laminated covering. The dimples are produced during fabrication of the laminated graft. During lamination, air is evacuated through small holes in the lamination mandrel. The holes may be for example approximately 0.030" diameter, The evacuation of the air leaves dimples in the ePTFE layer, which produce a discontinuity in the sinter and consolidation within the ePTFE. As will be further shown and described with reference to FIG. 3, the size and shape of the mandrel holes can be varied in order to alter the stress state in the finished graft upon bending. Due to the discontinuity, the dimpled region has a lower stiffness and permeability. In accordance with the present invention, the stiffness of the graft can therefore be controlled by exploiting the difference in the mechanical properties between the dimpled and non-dimpled areas, thereby creating a graft having greater flexibility in certain define regions. Graft 100, includes dimples arranged in various exemplary patterns.

Region 120 shows a circumferentially arranged pattern of dimples located at open end 110. The spacing, shape and size of each of the dimples may be varied to achieve a particular degree of flexibility in that region. Furthermore, the circumferentially arranged pattern is not limited to the open end, or any other location, of the graft, but may be disposed at any point where a degree of uniform flexibility around the circumference of the graft is needed.

Turning to region 122, an axial pattern of dimples is depicted. The axial pattern disposed the dimples in the axial direction to produce a lower stiffness in the axial direction. Therefore, the flexibility of the stent-graft is increased in alignment with the axial orientation. Any number of axially oriented rows of dimples can be added to the graft at various locations in order to impart the particular bending characteristics desired.

Region 124 depicts an undulating pattern of dimples, wherein the dimples are offset with respect to a particular stent member 208, but follow the undulating pattern of the stent member 208. In this way the stent member 208 is less constrained by the adjacent ePTFE and therefore the graft 100 has greater flexibility in that area. The pattern of dimples can follow to either or both sides of stent member 208, or additionally be placed along side the stent members in any sequence desired. For example, the dimples could be placed along each successive undulating stent members for any portion of graft 100, or along its entire length. Additionally, the dimples could be placed along alternate undulating stent members in any sequence, such as for example every second, third or fourth stent member to achieve the desired flexibility. These examples are not meant to be limiting and the dimples could be placed in any sequence along stent members to achieve a desired degree of flexibility. Furthermore, in the case of a stent having an alternate design not incorporating undulating members, the dimples may be placed adjacent to any number of stent members in accordance with the design or pattern of that particular design.

Regions 126 and 128 depict placement of the dimples in the region between successive stent members 210, 212, and 214. In the pattern of region 126, the dimples are placed in a radial orientation around the graft 100, adjacent to peaks 200 of undulating stent portion 131, within the region of longitudinal offset between successive stent portions 131. Region 128 depicts dimples placed in an orientation parallel to the undulating stent portions 131 within the region between stent members 212 and 214. In region 128, the dimples pattern are aligned in such a way so as to provide flexibility in locations that experience the highest tensile/shear stress and deformation upon stent-graft bending. Typically, those areas include region 128.

In general, the flexibility of the stent-graft 100 of the present invention may increase with an increasing number of the graft regions 120, 122, 124, 126 and 128. The flexibility of the stent-graft 100 of the present invention may also increase with decreasing number of undulating stent portions 131. It should be noted that the different regions depicted on graft 100 are meant to be illustrative of the possible flexibility regions. One or more than one region or pattern, may be included on any particular graft. Furthermore, the graft tubular wall 116 of graft 100 is an unfolded wall or graft, i.e., the graft is not bent or doubled up so that one part lies on another part of the same segment. Desirably, the graft wall 116 is a substantially smooth tubular wall that is free of folds, crimps, pleats and the like. Further, the graft tubular wall 116 is desirably a substantially continuous tubular wall, i.e., one that is free of slits, openings, apertures and the like.

Desirably, the stent 130 is made from any suitable implantable, biocompatible, bioabsorbable or biodegradable material, including without limitation nitinol, stainless steel, cobalt-based alloy such as Eigiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), polyphosphate ester) and the like.

Further, the stent 130 may have a composite construction, such as described found in U.S. Patent Application Publication 2002/0035396 A1, the contents of which is incorporated herein by reference. For example, the stent 130 may have an inner core of tantalum gold, platinum, iridium or combination of thereof and an outer member or layer of nitinol to provide a composite wire for improved radiocapacity or visibility. Alternatively, a radiopaque member or wire may be secured to a portion of the stent 130 for improved radiocapacity or visibility.

The graft 118 of the present invention may suitably be made from extruded, molded or cast polymeric materials. Nonlimiting examples of useful polymeric materials for the non-textile polymeric graft portions include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material polytetrafluoroethylene (PTFE), including expanded polytetrafluoroethylene (ePTFE).

PTFE exhibits superior biocompatibility and low thrombogenicity, which makes it particularly useful as vascular graft material in the repair or replacement of blood vessels or other bodily lumens. Desirably the non-textile layer is a tubular structure manufactured from ePTFE, The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. Such physically modified ePTFE material may be made by reorienting the node and fibril structure through the application of a radially expansive and longitudinally foreshortening force. The physically modified ePTFE tubular structure is able to be elongated or expanded and then returned to its original state without an elastic force existing therewithin. Additional details of the physically modified ePTFE and methods for making the same can be found in U.S. Pat. No. 6,716,239, the contents of which are incorporated by reference herein.

Figure 3A:
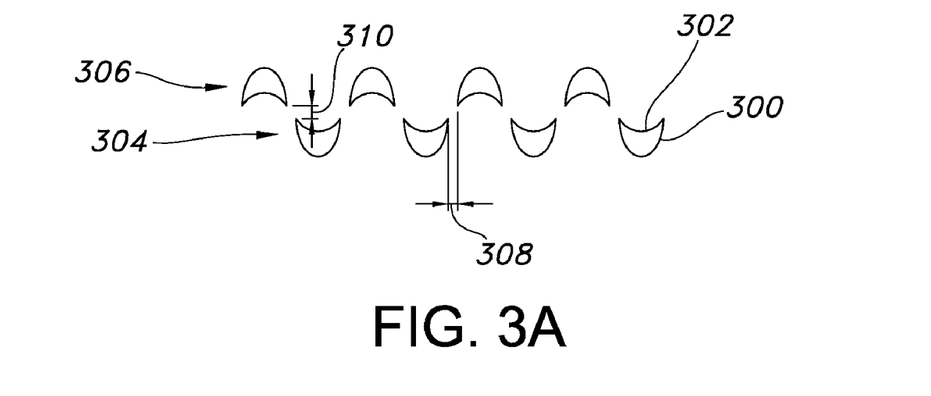
FIG. 3A, 3B, AND 3C shows a representation geometries for perforation holes of the endoluminal prosthesis of FIG. 1.

Turning now to FIG. 3 there is shown a an exemplary selection of mandrel hole geometries for use in forming dimples 101 in graft 100. By varying the shape of the mandrel holes the stress state in the finished graft can be altered upon bending of the graft. Shown in FIG. 3A, is a depiction of a pattern of semi-elliptical holes 300 for the dimple forming mandrel holes. The semi-elliptical holes are bisected by a concave shaped edge 302. The holes are aligned in two rows 304 and 306 wherein the concave shaped edge 302 of each hole 300 faces the opposing row. The holes are offset both longitudinally 308 and laterally 310. Both offset distances can be varied so as to achieve a particular dimple pattern and therefore flexibility. It should further be noted that while the holes 300 are shown having the concave edge 302 in opposition, the orientation of the holes can be varied in any pattern. For example, each hole can be varied independently or in groups. In one example, the holes could all be rotated 180 degrees so that the concave edge 302 of each hole faces the same direction, or face in opposite directions away from each other.

Figure 3B:
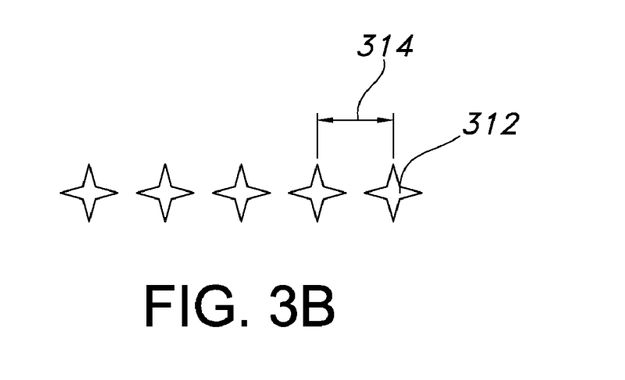

Turning now to FIG. 3B there is shown a depiction of a pattern of four pointed star shaped hole 312. The holes are offset longitudinally 314. The offset distances can be varied so as to achieve a particular dimple pattern and therefore flexibility. It should further be noted that while the holes 312 are shown having four points, however, the number of points can be varied to any number, both greater than four or less than four. Furthermore, the orientation of each hole can be varied independently or in groups.

Figure 3C:
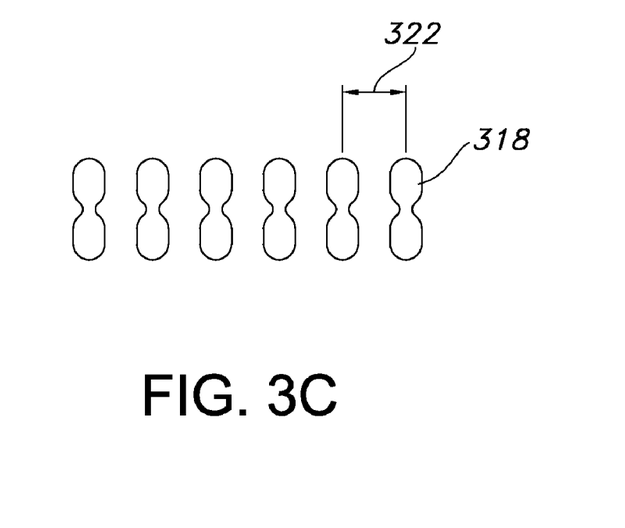

Turning now to FIG. 3C, there is shown a depiction of a pattern of oval shaped holes 318. The holes 318 have a constricted center portion 320 wherein the hole has a narrow longitudinal cross section. The holes are offset longitudinally 322. The offset distances can be varied so as to achieve a particular dimple pattern and therefore flexibility. It should further be noted that while the holes 318 are shown having a center constriction, the constriction need not be used, or may be placed in an alternate location along the lateral dimension of holes 318, additionally, more than one constriction can be placed on each hole. Furthermore, the orientation of each hole can be varied independently or in groups.

Figure 4:
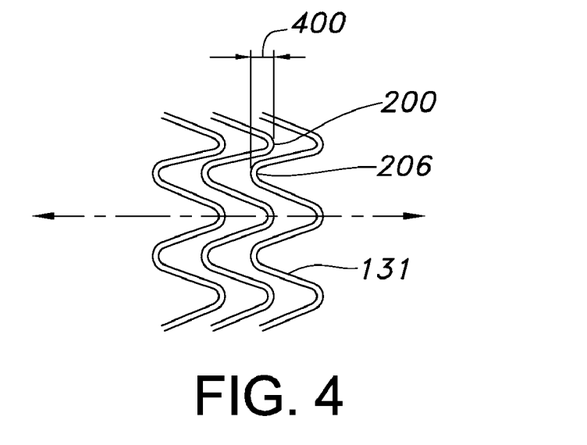
FIG. 4 is a partial exploded view of the stent of FIG. 1 further detailing the stent configuration.

Turning now to FIG. 4 there Is described a nested undulating stent portion 131 wherein, the valleys 206 of one undulating stent portion 131 may be longitudinally disposed within a circumferential plane defined by the peaks 200 of an adjacent undulating stent portion 131, and separated by an offset distance 400. Desirably, the offset distance 400, is less than the longitudinal length defined by the longitudinal distance from a peak 200 and a valley 206 of the undulating stent portion 131.

Figure 5:
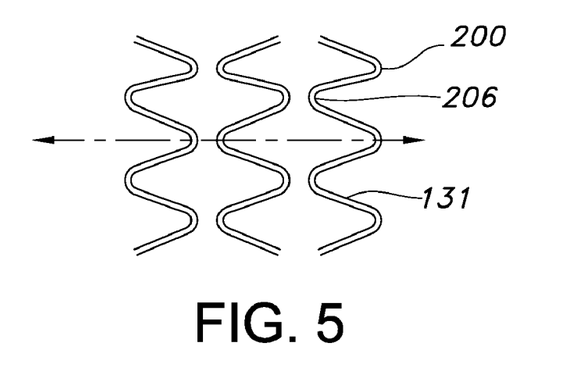
FIG. 5 is a partial exploded view of the stent of FIG. 1 further detailing the stent configuration.
Figure 6:
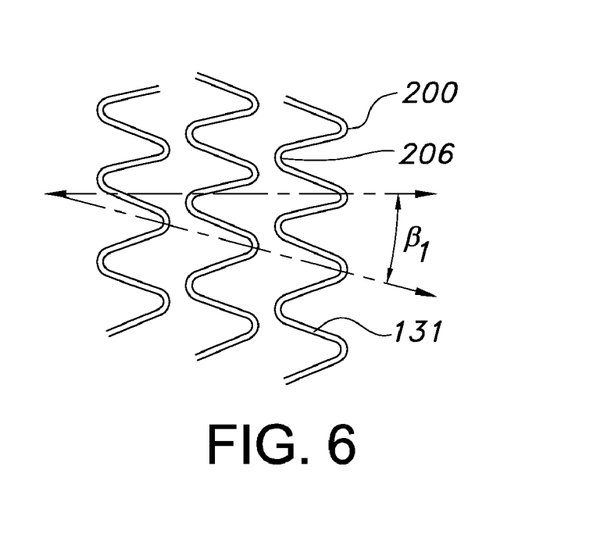
FIG. 6 is a partial exploded view of the stent of FIG. 1 further detailing the stent configuration.

The present invention, however, is not limited to undulating stent portions 131 having longitudinally aligned peaks 200 and valleys 206. For example, as depicted in FIG. 5, certain peaks 200 of adjacent undulating stent portions 131 may be proximally disposed relative to one and the other in the longitudinal direction while other peaks 200 are distally disposed to one and the other. As compared to FIG. 4, the peaks 200 and valleys 206 depicted in FIG. 5 are not in substantial longitudinal phase with one and the other. Moreover, as depicted in FIG. 6, the peaks 200 of adjacent undulating stent portions 131 may be offset from the longitudinal axis by an angle, for example by a angle of $\beta_1$. The degree of angular offsetting, i.e., $\beta_1$ may be suitably varied, for example from about 1° to about 45°, and need not be constant along the longitudinal length of the stent-graft 100 of the present invention.

The undulating stent portions 131 may comprise a single wire or wires that have been helically wound to form the stent 130. The wire or wires at the stent ends may be joined by welding, clamping and the like to form an atraumatic end or ends. In other word, the stent 130 of the present invention is desirably free or substantially free of loose wire ends at either or both of the open ends. The undulating stent portions 131 of the present invention are not limited to helically wound wire or wires, and such undulating stent portions 131 may be formed by other suitable methods. For example, the stent 130 with the undulating stent portions 131 may be machined from a stock of material, including a tubular stock. Such machining may include, without limitation, laser cutting, chemical etching, electrochemical etching, molding, and the like.

The polymeric graft 118 of the present invention may be secured to itself and/or secured to the stent 130 through, any suitable means, including without limitation lamination and/or adhesive bonding. The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent. Details of suitable bonding agents and methods for bonding are further described in U.S. Patent Application Publication Nos. 2003/0017775 A1 and 2004/0182511 A1, the contents of which are incorporated herein by reference.

With any embodiment, the stent-graft 100 may be used for a number of purposes including to maintain patency of a body lumen, vessel or conduit, such as in the coronary or peripheral vasculature, esophagus, trachea, bronchi, colon, biliary tract, urinary tract, prostate, brain, and the like. The devices of the present invention may also be used to support a weakened body lumen or to provide a fluid-tight conduit for a body lumen.

Also, the stent-graft 100 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents: and agents which interfere with endogenous vasoactive mechanisms.

Stent 10 may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, anti hemorrhagic agents, antihistamine agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists (e.g., CGS 21680, regadenoson, UK 432097 or GW 328267), serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof.

Useful non-genetic therapeutic agents for use in connection with the present invention include, but are not limited to, (a) anti-thrombotic agents such as heparin, heparin derivatives, urokinase, clopidogrel, and PPack (dextrophenylalanine proline arginine chloromethylketone);

(b) anti-inflammatory agents such as dexamethasone, prednisolone, corticosterone, budesonide, estrogen, sulfasalazine and mesalamine;

(c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;

(d) anesthetic agents such as lidocaine, bupivacaine and ropivacaine;

(e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;

(f) vascular cell growth promoters such as growth factors, transcriptional activators, and translational promoters;

(g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

(h) protein kinase and tyrosine kinase inhibitors (e.g., tyrphostins, genistein, quinoxalines);

(i) prostacyclin analogs;

(j) cholesterol-lowering agents;

(k) angiopoietins;

(l) antimicrobial agents such as triclosan, cephalosporins, aminoglycosides and nitrofurantoin;

(m) cytotoxic agents, cytostatic agents and cell proliferation affectors;

(n) vasodilating agents;

(o) agents that interfere with endogenous vasoactive mechanisms;

(p) inhibitors of leukocyte recruitment, such as monoclonal antibodies;

(q) cytokines;

(r) hormones;

(s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin;

(t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine);

(u) bARKct inhibitors;

(v) phospholamban inhibitors;

(w) Serca 2 gene/protein;
(x) immune response modifiers including aminoquizolines, for instance, imidazoquinolines such as resiquimod and imiquimod;
(y) human apolioproteins (e.g., AI, AII, AIII, AIV, AV, etc.);
(z) selective estrogen receptor modulators (SERMs) such as raloxifene, lasofoxifene, arzoxifene, miproxifene, ospemifene, PKS 3741, MF 101 and SR 16234;
(aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar;
(bb) prostaglandin E agonists, including PGE2 agonists, such as alprostadil or ONO 8815Ly;
(cc) thrombin receptor activating peptide (TRAP);
(dd) vasopeptidase inhibitors including benazepril, fosinopril, lisinopril, quinapril, ramipril, imidapril, delapril, moexipril and spirapril;
(ee) thymosin beta 4;
(ff) phospholipids including phosphorylcholine, phosphatidylinositol and phosphatidylcholine; and
(gg) VLA-4 antagonists and VCAM-1 antagonists, The non-genetic therapeutic agents may be used individually or in combination, including in combination with any of the agents described herein.

Further examples of non-genetic therapeutic agents, not necessarily exclusive of those listed above, include taxanes such as pacitaxel (including particulate forms thereof, for instance, protein-bound paciltaxel particles such as albumin-bound paciltaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Useful genetic therapeutic agents for use in connection with the present invention include, but are not limited to, anti-sense DNA and RNA as well as DNA coding for the various proteins (as well as the proteins themselves), such as (a) anti-sense RNA; (b) tRNA or rRNA to replace defective or deficient endogenous molecules; (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$ platelet-derived endothelial growth factor, platelet-derived growth factor, tumor necrosis factor $\alpha$, hepatocyte growth factor and insulin-like growth factor; (d) cell cycle inhibitors including CD inhibitors, and (e) thymidine kinase ("TK") and other agents useful for interfering with cell proliferation, DNA encoding for the family of bone morphogenic proteins ("BMP's") are also useful and include, but not limited to, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently desirably BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include, but not limited to, viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention may include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following:
(a) Ca-channel blockers including benzothiazapines such as diltiazem and clentiazem, dihydropyridines such as nifedipine, amlodipine and nicardapine, and phenylalkylamines such as verapamil;
(b) serotonin pathway modulators including: 5-HT antagonists such as ketanserin and naftidrofuryl, as well as 5-HT uptake inhibitors such as fluoxetine;
(c) cyclic nucleotide pathway agents including phosphodiesterase inhibitors such as cilostazoie and dipyridamole, adenylate/Guanylate cyclase stimulants such as forskolin, as well as adenosine analogs;
(d) catecholamine modulators including $\alpha$-antagonists such as prazosin and bunazosine, $\beta$-antagonists such as propranolol and $\alpha/\beta$-antagonists such as labetalol and carvedilol;
(e) endothelin receptor antagonists such as bosentan, sitaxsentan sodium, atrasentan, endonentan;
(f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine;
(g) Angiotensin Converting Enzyme (ACE) inhibitors such as cilazapril, fosinopril and enalapril;
(h) ATII-receptor antagonists such as saralasin and losartin;
(i) platelet adhesion inhibitors such as albumin and polyethylene oxide;

(j) platelet aggregation inhibitors including cilostazoie, aspirin and thienopyridine (ticlopidine, clopidogrel) and GP IIb/IIIa inhibitors such as abciximab, epitifibatide and tirofiban;
(k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C;
(l) cyclooxygenase pathway inhibitors such as aspirin, ibuprofen, flurbiprofen, indomethacin and sulfinpyrazone;
(m) natural and synthetic corticosteroids such as dexamethasone, prednisolone, methprednisolone and hydrocortisone;
(n) lipoxygenase pathway inhibitors such as nordihydroguairetic acid and caffeic acid;
(o) leukotriene receptor antagonists; (p) antagonists of E- and P-selectins;
(q) inhibitors of VCAM-1 and ICAM-1 interactions;
(r) prostaglandins and analogs thereof including prostaglandins such as PGE1 and PGI2 and prostacyclin analogs such as ciprostene, epoprostenol, carbacyclin, iloprost and beraprost;
(s) macrophage activation preventers including bisphosphonates;
(t) HMG-CoA reductase inhibitors such as lovastatin, pravastatin, atorvastatin, fluvastatin, simvastatin and cerivastatin;
(u) fish oils and omega-3-fatty acids;
(v) free-radical scavengers/antioxidants such as probucol, vitamins C and E, ebselen, trans-retinoic acid, SOD (orgotein) and SOD mimics, verteporfin, rostaporfin, AGI 1067, and M40419;
(w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives;
(x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518;
(y) cell motility inhibitors such as cytochalasin B;
(z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paciltaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin;
(aa) matrix deposition/organization pathway inhibitors such as halofuginone or other quinazolinone derivatives, pirfenidone and tranilast;
(bb) endothelialization facilitators such as VEGF and RGD peptide;
(cc) blood rheology modulators such as pentoxifylline and
(dd) glucose cross-link breakers such as alagebrium chloride (ALT-711).

These therapeutic agents may be used individually or in combination, including in combination with any of the agents described herein.

Numerous additional therapeutic agents useful for the practice of the present invention are also disclosed in U.S. Pat. No. 5,733,925 to Kunz, the contents of which is incorporated herein by reference.

A wide range of therapeutic agent loadings may used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

The invention being this described, it will now be evident to those skilled in the art that the invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An endoprosthesis comprising:
    a radially distensible, tubular stent comprising opposed open ends and a stent wall structure having opposed exterior and luminal surfaces; and
    a seamless tubular covering secured to one of said stent surfaces and extending in a longitudinal direction, said seamless tubular covering comprising laminated PTFE having a node and fibril structure, wherein the laminated PTFE comprises at least two laminated layers wherein said laminated layers include at least one region where a first laminated layer has a plurality of dimples and the first laminated layer is not securely bonded to a second laminated layer, said at least one region having a different bending flexibility from regions where the first laminated layer is securely bonded to the second laminated layer.

2. An endoprosthesis according to claim 1, wherein said tubular covering has a plurality of regions along the longitudinal direction of the tubular covering where the first laminated layer has a plurality of dimples.

3. An endoprosthesis according to claim 1, wherein said plurality of dimples are arranged in at least one predetermined pattern.

4. An endoprosthesis according to claim 1, wherein said plurality of dimples are arranged in more than one predetermined pattern.

5. An endoprosthesis according to claim 1, wherein said stent further comprises a longitudinal length and said stent has an expanded state and a contracted state, wherein the longitudinal length of the stent in the expanded state is substantially equal to the longitudinal length of the stent in the contracted state.

6. An endoprosthesis according to claim 1, wherein said stent is a self-expanding stent, a balloon-expandable stent or combinations thereof.

7. An endoprosthesis according to claim 1, wherein said stent comprises a biocompatible material selected from the group consisting of metallic materials, polymeric materials, bioabsorbable materials, biodegradable materials, and combinations thereof.

8. An endoprosthesis according to claim 1, wherein said stent comprises a plurality of undulating stent segments.

9. An endoprosthesis according to claim 1, wherein said stent comprises an undulating wire helically wound into a plurality of circumferential adjacent windings to define said stent wall structure.

10. An endoprosthesis according to claim 1, wherein said at least one region preferentially deforms when subjected to a bending stress as compared to other regions of said tubular covering.

* * * * *